United States Patent [19]

Iwai

[11] Patent Number: 5,874,568
[45] Date of Patent: Feb. 23, 1999

[54] COUPLING UNIT OF (6-4) PHOTOPRODUCT, PROCESS FOR PREPARING THE SAME, PROCESS FOR PREPARING OLIGONUCLEOTIDE CONTAINING (6-4) PHOTOPRODUCT BY USING THE SAME AND PROCESS FOR PREPARING DNA CONTAINING (6-4) PHOTOPRODUCT BY USING THE SAME

[75] Inventor: Shigenori Iwai, Osaka, Japan

[73] Assignee: Biomolecular Engineering Research Institute, Osaka, Japan

[21] Appl. No.: 783,986

[22] Filed: Jan. 15, 1997

[30] Foreign Application Priority Data

Jan. 31, 1996 [JP] Japan .................................. 8-015236
May 30, 1996 [JP] Japan .................................. 8-136272

[51] Int. Cl.$^6$ .................................................. C07H 21/04
[52] U.S. Cl. ...................... 536/25.34; 536/26.5; 536/26.8
[58] Field of Search .............................. 536/25.34, 26.5, 536/26.8

[56] References Cited

PUBLICATIONS

J.S. Taylor et al.: "A building block for the sequence–specific introduction of cis–syn thymine dimers into oligonucleotides" J. Am. Chem. Soc., vol. 109, 1987, pp. 6735–6742 (Issue No. 22).

T. Murata et al.: "Synthesis and characterization of a substrate for T4 endonuclease V containing a phosphorothioate linkage at the thymine dimer site" Nucleic Acids Res., vol. 18, 1990, pp. 7279–7286 (Issue No. 24).

Douki, T.; Voituriez, L.; Cadet, J.: "Characterization of the (6–4) photoproduct of 2'–deoxycytidylyl–(3' →5')–thymidine and of its Dewar valence isomer", Photochem. Photobiol., vol. 53, 1991, pp. 293–297 (Issue No. 3).

Reardon et al., "Comparative Analysis of Binding of Human Damaged DNA–binding Protein (XPE) and *Escherichia coli* Damage Recognition Protein (UvrA) to the Major Ultraviolet Products: T[c,s]T, T[t,s]T, T[6–4]T and T[Dewar]T," *J. Biol. Chem.*, 268(28), 21301–21308 (Oct. 5, 1993).

LeClerc et al., "The Thymine–Thymine Pyrimidine–Pyrimidone(6–4) Ultraviolet Light Photoproduct is Highly Mutagenic and Specifically Induces 3'–Thymine–to–Cytosine–Transitions in *Escherichia coli,*" *Proc. Nat. Acad. Sci. USA,* 88(21), 9685–9689 (Nov. 1991).

Todo et al., "A New Photoreactivating Enzyme That Specifically Repairs Ultraviolet Light–Induced (6–4)Photoproducts," *Nature,* 361, 371–374 (Jan. 28, 1993).

Galloway et al., "Metabolic Processing of Cyclobutyl Pyrimidine Dimers and (6–4) Photoproducts in UV–Treated Human Cells," *J. Biol. Chem.,* 269(2), 974–980 (Jan. 14, 1994).

Kim et al., "Characterization of (6–4) Photoproducts DNA Photolyase," *J. Biol. Chem.,* 269(11), 8535–8540 (Mar. 11, 1994).

Zhao et al., "Eliciting DNA Photoproduct–Specific Antibodies With A Dinucleotide Photoproduct Antigen," *J. Amer. Chem. Soc.,* 116(20), 8870–8876 (Oct. 5, 1994).

Hwang et al., "NMR Structural Studies of DNA Decamer Duplex Containing the Dewar Photoproduct of Thymidylyl(3'→5')thymidine—Conformational Changes of the Oligonucleotide Duplex By Photoconversion of a(6–4) Adduct to Its Dewar Valence Isomer," *Eur. J. Biochem.,* 235(1/2) 359–365 (Jan. 1996).

Taylor et al., "Solution–State Structure of the Dewar Pyrimidinone Photoproduct of Thymidylyl–(3'→5')–thymidine," *Biochemistry,* 27(19), 7206–7215 (Sep. 20, 1988).

Bérubé et al., "Thermospray High–Performance Liquid Chromatographic Mass Spectral Analyses of the Photoproducts of dTpdT and dTpdU," *Biological Mass Spectrometry,* 21, 259–266 (1992).

Douki et al., "Formation of Cyclobutane Dimers and (6–4) Photoproducts Upon Far–UV Photolysis of 5–Methhylcytodine–Containing Dinucleoside Monophosphates," *Biochemistry,* 33(39), 11942–11950 (Oct. 4, 1994).

(List continued on next page.)

*Primary Examiner*—Marian C. Knode
*Assistant Examiner*—L. Eric Crane
*Attorney, Agent, or Firm*—Jordan and Hamburg

[57] ABSTRACT

A coupling unit of a (6-4) photoproduct represented by the formula (I):

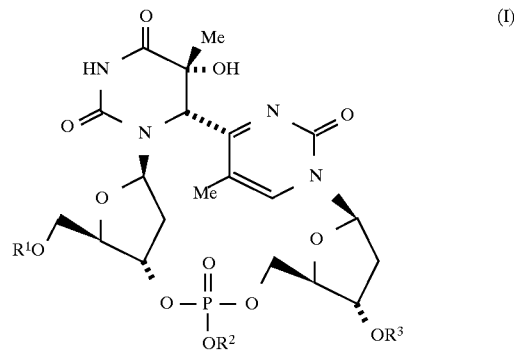

wherein R$^1$ represents a protective group, R$^2$ represents a methyl group or a 2-cyanoethyl group, and R$^3$ represents

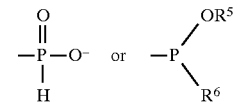

wherein R$^5$ represents a methyl group or a 2-cyanoethyl group, and R$^6$ represents a —N(R')(R") group, a N-morpholino group, a N-pyrrolidinyl group or a 2,2,6,6-tetramethyl-N-piperidyl group where R' and R" each represent a lower alkyl group, a process for preparing the same, a process for preparing an oligonucleotide containing a (6-4) photoproduct by using the same, and a process for preparing DNA containing a (6-4) photoproduct by using the same are disclosed.

13 Claims, No Drawings

PUBLICATIONS

Smith et al., "Preparation and Characterization of a Set of Deoxyoligonucleotide 49–mers Containing Site–Specific Cis–syn, Trans–syn–I, (6–4), and Dewar Photoproducts of Thymidylyl(3'→5')–thymidine," *J. Biol. Chem.,* 268(15), 11143–11151 (May 25, 1993).

Liu et al., "Remarkable Photoreversal of a Thio Analog of the Dewar Valence Isomer of the (6–4) Photoproduct of DNA to the Parent Nucleotides," *J. Amer. Chem. Soc.,* 118(13), 3287–3288 (Apr. 3, 1996).

Iwai et al., "Synthesis of a Phosphoramidite Coupling Unit of the Pyrimidine (6–4) Pyrimidone Photoproduct And Its Incorporation Into Oligodeoxynucleotides," *J. Amer. Chem. Soc.,* 118(32), 7642–7643 (Aug. 14, 1996).

COUPLING UNIT OF (6-4) PHOTOPRODUCT, PROCESS FOR PREPARING THE SAME, PROCESS FOR PREPARING OLIGONUCLEOTIDE CONTAINING (6-4) PHOTOPRODUCT BY USING THE SAME AND PROCESS FOR PREPARING DNA CONTAINING (6-4) PHOTOPRODUCT BY USING THE SAME

BACKGROUND OF THE INVENTION

This invention relates to the synthesis of oligonucleotides containing a (6-4) photoproduct, a lesion at base moieties generated by irradiation of DNA in vivo with UV light. Such lesions in DNA induce genetic mutations and cause cellular death and transformation. In spite of such a risk, normal transmission of genetic information is generally maintained because organisms have some DNA-repairing systems in cells (Annu. Rev. Biochem., Vol. 65, pp. 135 to 167 (1996)). Not only the (6-4) photoproduct synthesized by the process of the present invention and DNA containing the same can be used in studies for elucidating the mechanisms of mutations and repair of DNA, but also they are useful as a reagent for clinical tests, such as production of antibodies detecting damaged DNA.

When DNA is irradiated with UV light, two types of major lesions are formed at the sites of adjacent pyrimidine bases. One of them is the cis-syn cyclobutane pyrimidine dimer, and the other is the pyrimidine (6-4) pyrimidone photoproduct (hereinafter referred to as "a (6-4) photoproduct"). It has been known that the (6-4) photo-product in DNA has the following structure and causes mutations with high frequency (see Proc. Natl. Acad. Sci. USA, vol. 88, pp. 9685 to 9689 (1991) and J. Mol. Biol., vol. 235, pp. 465 to 471 (1994)).

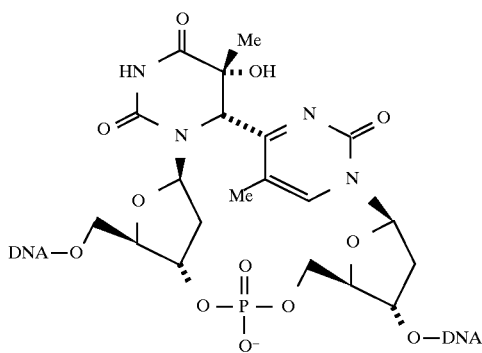

In previous studies, plasmid DNA irradiated with UV light has been used for the experiments of mutation and repair of DNA. However, it has been reported that various lesions including formamidopyrimidines are generated by UV light (Biochemistry, vol. 34, pp. 737 to 742 (1995)). Therefore, for detailed studies, it is necessary to use DNA having a specific lesion at a specific single site.

In previous reports on the preparation of damaged DNA, extremely short DNA fragments containing adjacent pyrimidines only at one site were irradiated with UV light, and from the reaction mixture, desired DNA containing the (6-4) photoproduct was purified by HPLC (high performance liquid chromatography) (J. Biol. Chem., vol. 268, pp. 11143 to 11151 (1993)). However, this process has the following disadvantages which reduce its practicality. Firstly, DNA obtained by this process has large limitations in the chain length and the base sequence, and its length is limited up to about a decamer. Secondly, the yield of the desired DNA is extremely low. Thirdly, the reaction mixture contains a Dewar isomer which is isomerized from the (6-4) photoproduct by exposure to the near UV light, and separation of this isomer is difficult (J. Biol. Chem., vol. 268, pp. 11143 to 11151 (1993)).

SUMMARY OF THE INVENTION

An object of the present invention is to provide a process for synthesizing a coupling unit of a (6-4) photoproduct and synthesizing DNA containing a (6-4) photoproduct by using the same. By the novel synthetic method, all of the problems in the conventional process have been solved, and DNA containing a (6-4) photoproduct at a specific position and having an optional length and base sequence can be synthesized with a high yield.

That is, the present invention relates to a coupling unit of a (6-4) photoproduct represented by the formula (I):

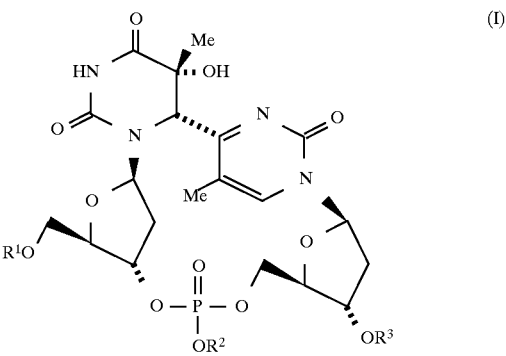

wherein $R^1$ represents a protective group, $R^2$ represents a methyl group or a 2-cyanoethyl group, and $R^3$ represents

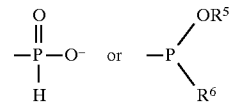

wherein $R^5$ represents a methyl group or a 2-cyanoethyl group, and $R^6$ represents a —N(R')(R") group, a N-morpholino group, a N-pyrrolidinyl group or a 2,2,6,6-tetramethyl-N-piperidyl group where R' and R" each represent a lower alkyl group, a process for preparing the coupling unit of the (6-4) photoproduct with the above formula (I), which is obtained by allowing a compound represented by the formula (V):

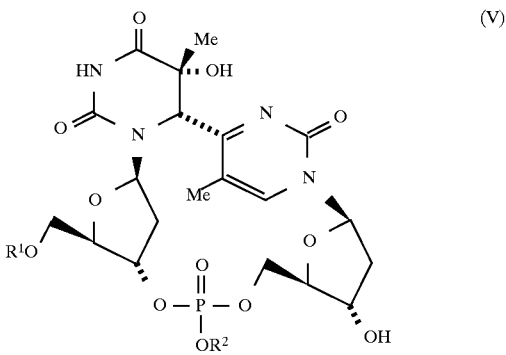

wherein $R^1$ and $R^2$ are the same as defined above to react with a compound represented by

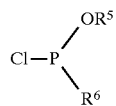

wherein $R^5$ and $R^6$ are the same as defined above, or allowing the compound represented by the formula (V) to react with tri(1,2,4-triazol-1-yl)phosphine, followed by hydrolysis;

a process for preparing the coupling unit of the (6-4) photoproduct with the above formula (I), which comprises:

(1) irradiating a thymidine dimer represented by the formula (II):

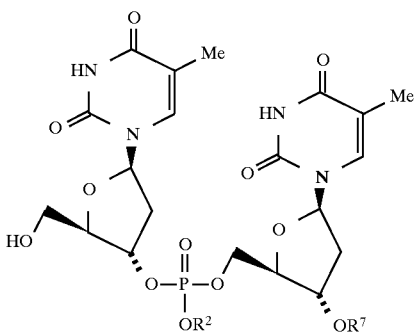

wherein $R^2$ is the same as defined above, and $R^7$ represents a levulinyl group or a t-butyldimethylsilyl group with UV light to obtain a (6-4) photoproduct represented by the formula (III):

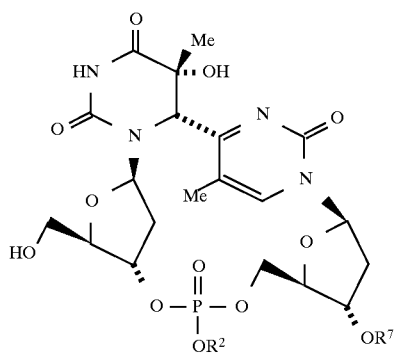

wherein $R^2$ and $R^7$ are the same as defined above;

(2) protecting the 5'—OH group to prepare a compound with the formula (IV):

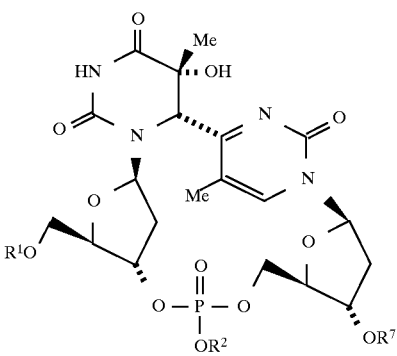

wherein $R^1$, $R^2$ and $R^7$ are the same as defined above;

(3) removing the protective group $R^7$ for the 3'—OH to obtain a compound with the formula (V):

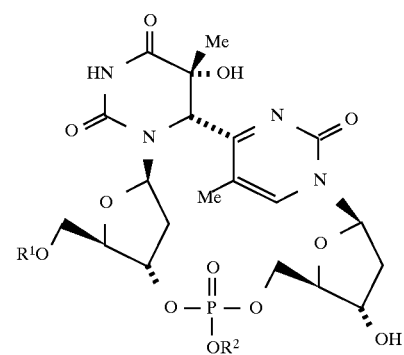

wherein $R^1$ and $R^2$ are the same as defined above; and (4) allowing the compound represented by the formula (V) to react with a compound represented by

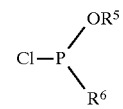

wherein $R^5$ and $R^6$ are the same as defined above, or allowing the compound represented by the formula (V) to react with tri(1,2,4-triazol-1-yl)phosphine, followed by hydrolysis;

a process for preparing an oligonucleotide containing a (6-4) photoproduct represented by the formula (X):

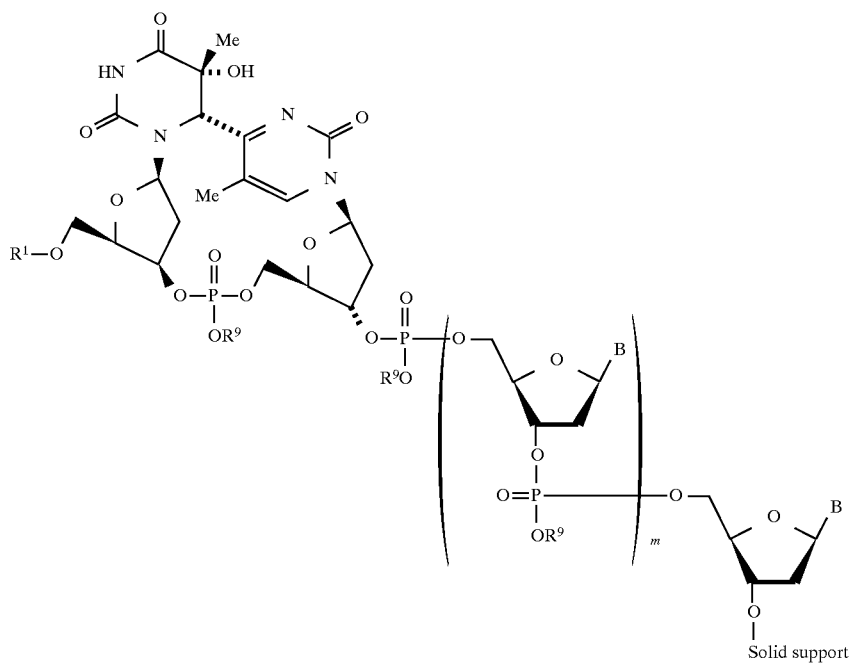

wherein $R^1$ is the same as defined above, $R^9$ represents a hydrogen atom, a methyl group or a 2-cyanoethyl group, B represents

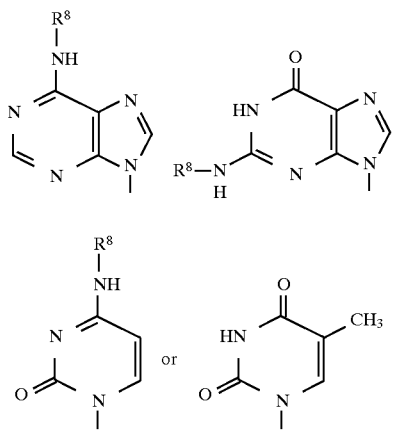

where $R^8$ represents a protective group, and m represents 1 to 30, which comprises:

(1) removing the protective group $R^1$ on an oligonucleotide linked to a solid support, represented by the formula (IX):

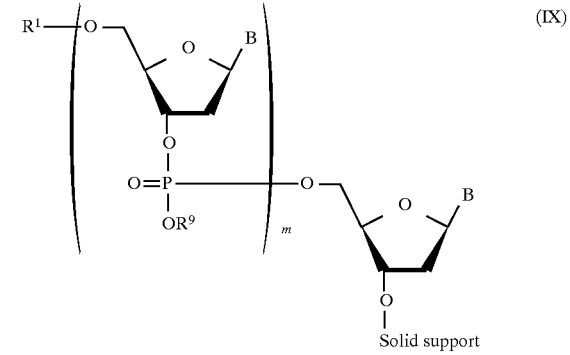

wherein $R^1$, $R^9$, B and m are the same as defined above;

(2) allowing the oligonucleotide to react with a coupling unit of a (6-4) photoproduct represented by the above formula (I), and (3) oxidizing the reaction mixture;

and a process for preparing DNA containing a (6-4) photoproduct represented by the formula (XII):

(XII)

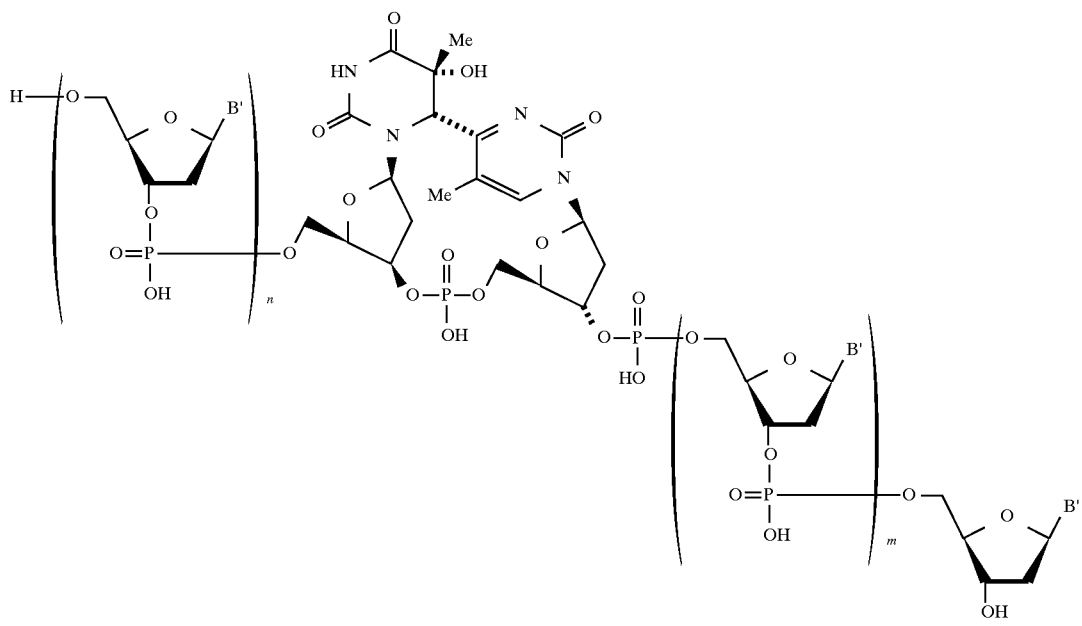

wherein B' represents

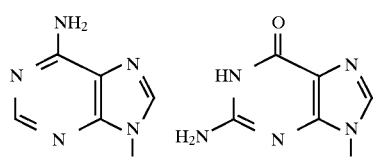

or

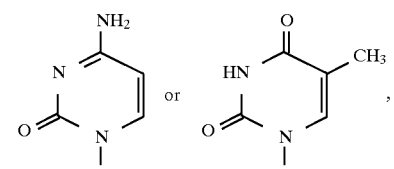

, m represents 1 to 30, and n represents 1 to 30, which comprises:

(1) allowing a nucleoside linked to a solid support, represented by the formula (VII):

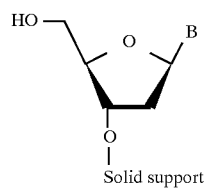

wherein B is the same as defined above, to react with a nucleotide represented by the formula (VIII):

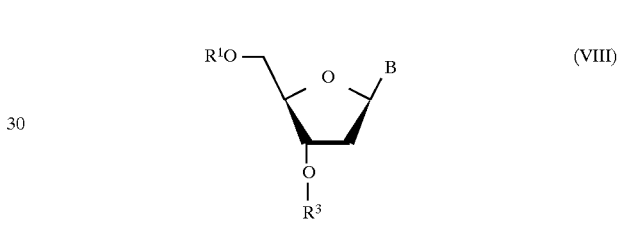

wherein $R^1$, $R^3$ and B are the same as defined above, oxidizing the reaction mixture and repeating removal of $R^1$, the above reaction, and oxidation to obtain an oligonucleotide represented by the formula (IX):

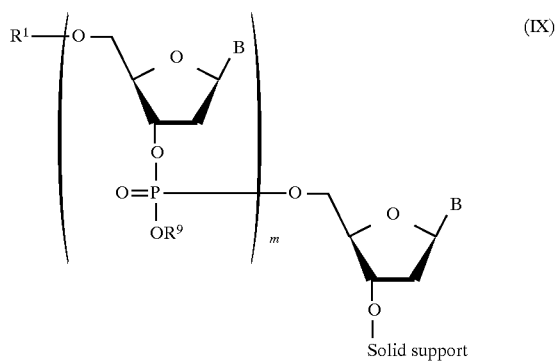

wherein $R^1$, $R^9$, B and m are the same as defined above;

(2) after removing the protective group $R^1$, allowing the oligonucleotide to react with the coupling unit of a (6-4) photoproduct represented by the above formula (I), and oxidizing the reaction mixture to obtain an oligonucleotide containing a (6-4) photoproduct represented by the formula (X):

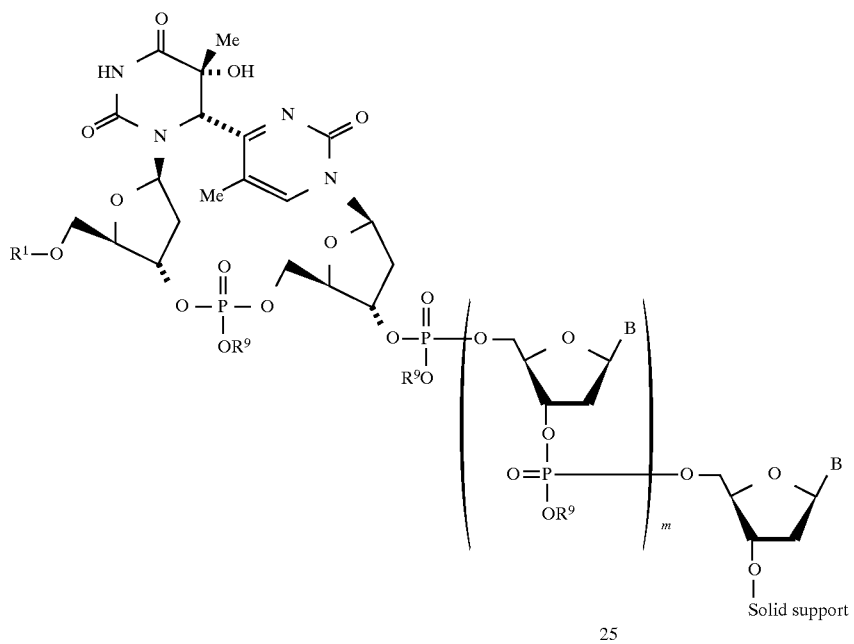

(X)

wherein $R^1$, $R^9$, B and m are the same as defined above;

(3) after removing the protective group $R^1$, allowing the oligonucleotide to react with the nucleotide represented by the formula (VIII), oxidizing the reaction mixture and repeating the reaction and oxidation to obtain a long oligonucleotide containing a (6-4) photoproduct represented by the formula (XI):

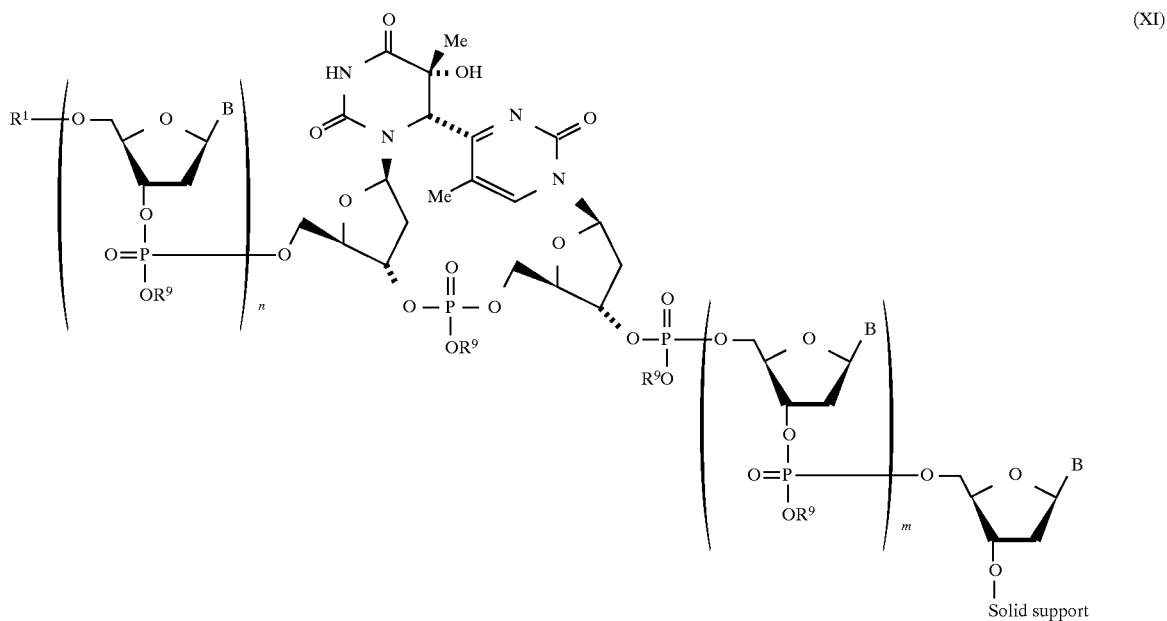

(XI)

wherein $R^1$, $R^9$, B, m and n are the same as defined above; and (4) after taking off the protective group $R^1$, treating the long oligonucleotide with aqueous ammonia to remove the protective groups $R^9$ and $R^8$ and simultaneously to cleave the long oligonucleotide from the solid support.

DETAILED DESCRIPTION OF THE INVENTION

In the following, the present invention is explained in detail.

The coupling unit of the (6-4) photoproduct of the present invention has the above formula (I).

As the protective group of $R^1$, any protective group used for synthesis of DNA may be used, including the 4,4'-dimethoxytrityl group which has been used most generally, and also the 4-methoxytrityl and 9-phenylxanthen-9-yl groups.

As $R^2$, a 2-cyanoethyl group is preferred.

By using H-phosphonate or phosphoramidite of

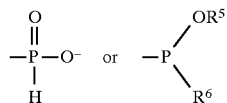

$R^3$, synthesis of DNA can be carried out. $R^5$ is a methyl group or a 2-cyanoethyl group, and a 2-cyanoethyl group is preferred. $R^6$ is a —N(R')(R") group, a N-morpholino group, a N-pyrrolidinyl group or a 2,2,6,6-tetramethyl-N-piperidyl group where R' and R" each represent a lower alkyl group, and a —N(R') (R") group is preferred. As R' and R" which may be the same or different from each other, a straight or branched lower alkyl group having 1 to 6 carbon atoms, preferably 1 to 3 carbon atoms such as a methyl group, an ethyl group, an n-propyl group and an isopropyl group may be mentioned. $R^3$ is preferably 2-cyanoethyl-N,N-dialkyl-phosphoramidite in which $R^5$ is a 2-cyanoethyl group and $R^6$ is a —N(R')(R") group. As N,N-dialkyl, N,N-dimethyl, N,N-diethyl, N,N-diisopropyl and N-methyl-N-isopropyl can be used. Most preferred as $R^3$ is 2-cyanoethyl-N,N-diiso-propylphosphoramidite.

The coupling unit with the formula (I) is synthesized by the following steps.

(1) A thymidine dimer represented by the above formula (II) is irradiated with UV light to obtain a protected (6-4) photoproduct represented by the above formula (III).

As $R^7$, a levulinyl group or a t-butyldimethylsilyl group is mentioned, and a levulinyl group is preferred. A synthetic method of 3'-levulinyl[thymidinyl(3'-5')thymidine] (2-cyano-ethyl)phosphotriester with the formula (II) is described in Nucleic Acid Res., vol. 18, pp. 7279 to 7286 (1990). In the compound with the formula (II), two kinds of diastereomers due to chirality of phosphorus are generated, and either of the diastereomers or a mixture thereof may be used.

When an aqueous acetonitrile solution containing the compound (1) described below was irradiated to a 1M solution of (II) with UV light (mainly at 254 nm) in a UV-cross-linker under the conditions of preferably 0° to 20° C. with 15 to 30 kJ, two peaks of products having an absorption maximum at 326 nm with shorter retention times than those of starting materials were detected by HPLC analysis. These peaks almost reached a plateau at a UV dose of 30 J/cm². Therefore, a photoreaction was carried out on a large scale by using the above conditions, and the reaction mixture was purified by reverse-phase partition chromatography to obtain a protected (6-4) photoproduct. This product has a UV absorption spectrum which is peculiar to the (6-4) photoproduct which has already been reported (J. Biol. Chem., vol. 257, pp. 13535 to 13543 (1982)), and its structure was confirmed by NMR spectroscopy and mass spectrometry.

(2) Next, the protective group $R^1$ is introduced onto a 5'—OH group of the (6-4) photoproduct with the formula (III) to obtain a compound with the above formula (IV).

For introducing a 4,4'-dimethoxytrityl group as the protective group $R^1$, 4,4'-dimethoxytrityl chloride is used in an amount of preferably 1.5 to 3 equivalent based on the amount of the (6-4) photoproduct with the formula (III) preferably at 0° to 40° C. for 1 to 6 hours.

(3) Next, the protective group $R^7$ for a 3'—OH group is removed to obtain a compound with the above formula (V).

The protective group $R^7$ can be removed with ammonia when $R^7$ is a levulinyl group, but in order to prevent elimination of the 2-cyanoethyl group of $R^2$, it is preferred to use hydrazine in an amount of preferably 1.5 to 10 equivalent based on the amount of the compound with the formula (IV) at 0° to 40° C. for 5 to 60 minutes. When $R^7$ is t-butyldi-methylsilyl, it can be removed with a fluoride ion, but the (6-4) photoproduct is partially decomposed.

(4) Finally, the compound with the formula (V) which lacks the $R^7$ group at 3'-position is allowed to react with a compound represented by

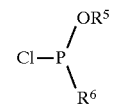

wherein $R^5$ and $R^6$ are the same as defined above, in an amount of 1.5 to 2 equivalents based on the amount of the compound with the formula (V) at 0° to 40° C. for 30 to 90 minutes, or allowing the compound with the formula (V) to react with tri(1,2,4-triazol-1-yl) phosphine in an amount of 2 to 6 equivalents based on the amount of the compound with the formula (V) at 0° to 40° C. for 10 to 30 minutes, followed by hydrolysis, to introduce $R^3$ onto a 3'—OH group, whereby the desired coupling unit with the formula (I) is obtained.

DNA containing the (6-4) photoproduct with the formula (I) is prepared by using a DNA synthesizer according to the following steps.

(1) A nucleoside linked to a solid support, represented by the above formula (VI), means one of the four nucleosides in which a base moiety is protected, i.e., deoxyadenosine, deoxyguanosine, deoxycytidine or thymidine, and a nucleoside with the above formula (VII) in which the protective group $R^1$ is removed by trichloroacetic acid or the like according to a conventional method is a starting material.

As the protective group $R^8$, the t-butylphenoxyacetyl, isopropylphenoxyacetyl, phenoxyacetyl, and dimethylformamidino groups may be used.

The nucleoside represented by the formula (VII) is allowed to react with a nucleotide represented by the above formula (VIII). When the nucleotide is 2-cyanoethyl-N,N-dialkyl-phosphoramidite, this reaction is carried out in the presence of tetrazole. The phosphoramidite activated by tetrazole is allowed to react with the 5'—OH group and then with an oxidizer such as iodine to be converted into a pentavalent phosphotriester. When the nucleotide is H-phosphonate, it is activated with pivaloyl chloride and allowed to react with the nucleotide with the formula (VIII) repeatedly and then oxidized with iodine.

The reaction with the nucleotide with the formula (VIII) is repeated to obtain an oligonucleotide represented by the above formula (IX).

(2) Next, after the oligonucleotide with the formula (IX) is allowed to react with trichloroacetic acid to remove the protective group $R^1$, the oligonucleotide is allowed to react with the coupling unit of the (6-4) photoproduct with the formula (I) to obtain an oligonucleotide containing the (6-4) photoproduct represented by the above formula (X).

(3) For further chain elongating, the oligonucleotide is allowed to react with the nucleotide with the formula (VIII) in the same manner as described above (2), after the protective group $R^1$ in the oligonucleotide with the formula (X) is removed, to obtain a long oligonucleotide containing a desired (6-4) photoproduct represented by the above formula (XI).

(4) After the protective group $R^1$ in the oligonucleotide with the formula (XI) is taken off with trichloroacetic acid, the oligonucleotide is treated with aqueous ammonia to remove the protective groups $R^9$ and $R^8$ in B and to cleave the oligonucleotide from the solid support to obtain DNA containing the (6-4) photoproduct represented by the above formula (XII).

When an 8-mer synthesized by the above method (d(GTAT(6-4)TATG, SEQ ID NO:2) was analyzed by HPLC, a peak having a retention time and absorption maxima at 256 and 327 nm which were exactly the same as those of a (6-4) 8-mer prepared by the conventional process, was obtained as a main product. When the product was purified by preparative chromatography, the yield was 6.8 $A_{260}$ units (0.10 μmol), and this result showed that the product was obtained with a yield which was about 8 times higher than that of the conventional process. When the product was partially converted into an 8-mer containing the Dewar isomer and then analyzed, it was found that in this synthetic process, impurities of the Dewar isomer were not contained in the mixture before purification.

Using this process, a 30-mer (d(CTCGTCAGCATCT(6-4)TCATCATACAGTCAGTG, SEQ ID NO.1) containing the (6-4) photoproduct was synthesized. As a result, a peak having an absorption maximum in the long wavelength region was obtained as a main product in the same way as the 8-mer case. In the analysis using an anion-exchange column, this product was eluted at the same retention time as that of a 30-mer containing two thymines in place of the (6-4) photoproduct. The yield of the pure (6-4) 30-mer obtained after purification was 6.0 $A_{260}$ units.

EXAMPLES

The present invention is described in detail by referring to Examples.

Thin layer chromatography was carried out on Kieselgel 60 $F_{254}$ plates (trade name, manufactured by Merck Co.), using chloroform-methanol as a developing solvent. For column chromatography, either Wakogel C-200 or C-300 (trade name, manufactured by Wako Pure Chemical Industries) was used.

UV and visible spectra were measured by using a Beckman DU-64 spectrophotometer (trade name, manufactured by Beckman Co.)

$^1$H-NMR was measured by using a Bruker DMX600 apparatus (trade name, manufactured by Bruker Co.), using tetramethylsilane as an internal standard. $^{31}$P-NMR was measured by using a Bruker DPX300 apparatus (trade name, manufactured by Bruker Co.), using trimethyl phosphate as an internal standard.

Mass spectra (FABHRMS) were measured by using a JEOL JMS-AX500 or JMS-SX102A mass-spectrometer (trade name, manufactured by Japan Electro Optical Co.).

Oligonucleotides were synthesized by using an Applied Biosystems 394 Model DNA/RNA synthesizer (trade name, manufactured by Perkin Elmer Applied Biosystems).

For HPLC, an apparatus of Gilson was used, and analysis was carried out by using a Waters 996 photodiode array detector (trade name, manufactured by Waters Co.). As a column for reverse-phase analysis, Waters μ Bondasphere C18 300 Å (trade name, manufactured by Waters Co., an inner diameter of 3.9 mm×a length of 150 mm) was used, as a reverse-phase preparative column, Waters μ Bondapak C18 (trade name, manufactured by Waters Co., an inner diameter of 7.8 mm×a length of 300 mm) was used, and for anion-exchange analysis, a Tosoh TSK-GEL DEAE-2SW column (trade name, manufactured by Tosoh Corporation, Japan, an inner diameter of 4.6 mm×a length of 250 mm) were used. As a mobile phase, a linear gradient of acetonitrile in a 0.1M triethylammonium acetate buffer (pH 7.0) and that of ammonium formate in 20% aqueous acetonitrile was used for the reverse-phase and anion-exchange analyses, respectively.

Example 1

(i) Synthesis of Compound (2)

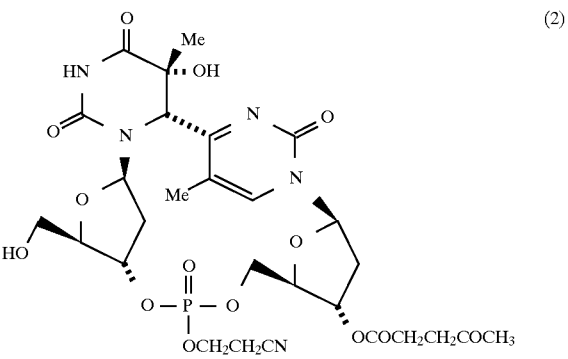

3'-Levulinyl[thymidilyl(3'-5')thymidine](2-cyanoethyl)-phosphotriester (1) having the following formula:

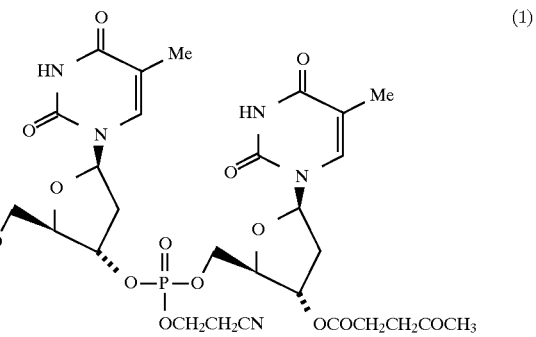

was synthesized according to Nucleic Acids Res., vol. 18, pp. 7279 to 7286 (1990). A 1 mM solution of the compound (1) in 20% aqueous acetonitrile (150 ml) was placed in an ice-cooled aluminum tray (23 cm×32 cm) and irradiated with UV light for 2 hours in a UV-crosslinker (Funakoshi FS-1500, trade name, manufactured by Funakoshi Co.) (the UV dose was ca. 30 J/cm$^2$). A solution obtained by repeating this operation 23 times (3.45 1) was concentrated and then divided into two portions, and each portion was purified by reverse-phase partition chromatography using a column (an inner diameter of 1.5 cm×a length of 28 cm) of C18 silica gel (Waters Preparative C18 125 Å, trade name, produced by Waters Co.). The eluted peak was analyzed by HPLC with a linear gradient (10 to 25%) of acetonitrile, and the solvent was evaporated to obtain a glassy title compound (2).

Yield: 0.39 g (0.55 mmol, 16%) TLC (chloroform : methanol=5:1): $R_f$0.35 UV (H$_2$O) λmax: 326 nm (ε=7.3× 10$^3$) $^1$H—NMR (600 MHz, pyridine-d$_5$) δ: 12.59 (s, 1H, —NH—), 8.01 (s, 1H, pT H6), 7.03 (m, 1H, pT H1'), 6.87 (d, J=8.55 Hz, 1H, Tp H1'), 5.75 (br, 2H, Tp H6, pT H3'), 4.98 (m, 1H, Tp H3'), 4.51 to 4.40 (m, 3H, pT H5', —OCH$_2$CH$_2$CN), 4.33 (m, 2H, Tp H5', pT H4'), 4.22 (m, 2H, Tp H5", pT H5"), 3.87 (m, 1H, Tp H4'), 3.11 (m, 1H, pT H2'), 3.02 (m, 2H, —OCH$_2$CH$_2$CN), 2.76 (m, 2H, —OCOCH$_2$CH$_2$CO—), 2.74 (s, 3H, pT —CH$_3$), 2.68 (m, 1H, pT H2"), 2.64 (m, 1H, 5'—OH), 2.15 (m, 4H, Tp H2', H2", —OCOCH$_2$CH$_2$CO—), 2.08 (s, 3H, —CH$_2$COCH$_3$), 1.88 (s, 3H, Tp, —CH$_3$) $^{31}$P—NMR (121.5 MHz, pyridine-d$_5$) δ: -3.72 ppm FABHRMS m/z: 697.1990 (M$^-$, C$_{28}$H$_{36}$O$_{14}$N$_5$P required 697.1996)

(ii) Synthesis of Compound (3)

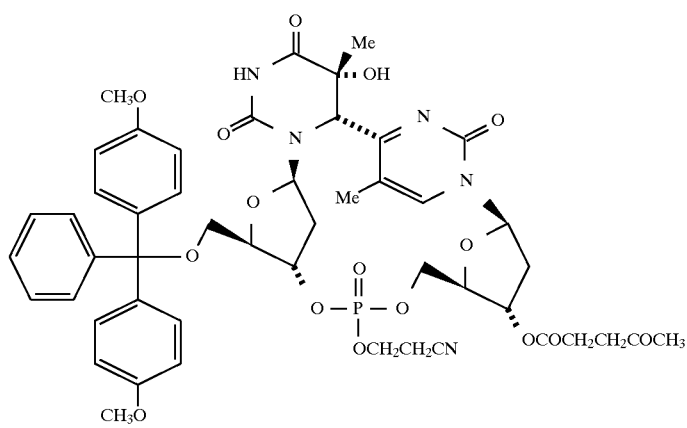

(3)

The compound (2) obtained in Example 1 (i) (352 mg (504 μmol)) was dissolved in 6 ml of pyridine, 427 mg (1.26 mmol) of 4,4'-dimethoxytrityl chloride was added to the solution, and the mixture was stirred at room temperature for 3 hours. Thereafter, a small amount of methanol was added, and the mixture was concentrated. After 30 ml of chloroform was added to the concentrate and the mixture was washed with water, the solvent was evaporated. The residue was purified on a silica gel column (a product was eluted with 3% methanol : chloroform), and the solvent was evaporated to obtain a foamy compound (3) with $R_f$ 0.30 (chloroform : methanol=10 : 1).

Yield: 421 mg (421 μmol, 84%) TLC (chloroform : methanol=10 : 1): $R_f$ 0.30 $^1$H-NMR (600 MHz, acetone-$d_6$) δ (ppm): 9.55 (s, 1H, —NH—) 7.78 (s, 1H, pT H6), 7.56 (d, J=7.3 Hz, 2H, aromatic ring), 7.43 (d, J=5.94 Hz, 2H, aromatic ring), 7.42 (d, J=5.93Hz, 2H, aromatic ring), 7.36 (dd, J=7.80, 7.80Hz, 2H, aromatic ring), 7.26 (dd, J=7.34, 7.34 Hz, 1H, aromatic ring), 6.93 (d, J=8.94 Hz, 4H, aromatic ring), 6.61 (dd, J=5.05, 7.39 Hz, 1H, pT H1'), 6.28 (dd, J=1.66, 8.73 Hz, 1H, Tp H1'), 5.44 (m, 1H, pT H3'), 5.09 (s, 1H, Tp H6), 4.70 (s, 1H, —OH), 4.16 to 4.01 (m, 6H, pT H4', H5', H5", Tp H3', —OCH$_2$CH$_2$CN) 3.96 (m, 1H, Tp H4'), 3.81 (s, 6H, —OCH$_3$), 3.60 (dd, J=2.11, 10.71 Hz, 1H, Tp H5'), 3.30 (dd, J=7.03, 10.72 Hz, 1H, Tp H5"), 3.05 (m, 1H, pT H2'), 2.89 to 2.77 (m, —OCH$_2$CH$_2$CN, —OCOCH$_2$CH$_2$CO—), 2.62 (m, 1H, pT H2"), 2.57 (m, 2H, —OCOCH$_2$CH$_2$CO—), 2.14 (m, 1H, Tp H2"), 2.13 (s, 3H, —COCH$_3$), 1.99 (S, 3H, pT —CH$_3$), 1.67 (s, 3H, Tp —CH$_3$), 1.61 (m, 1H, Tp H2') $^{31}$P—NMR (121.5 MHz, acetone-$d_6$) δ: -3.53 ppm (iii) Synthesis of Compound (5)

The compound (3) obtained in Example 1 (ii) (239 mg (239 μmol)) was dissolved in 2.5 ml of pyridine, 3.0 ml of a solution containing 116 μl of hydrazine monohydrate in pyridine-acetic acid (3:2) was added to the solution, and the mixture was stirred at room temperature for 5 minutes. Then, under ice cooling, 1.0 ml of acetone was added to the mixture. The resulting mixture was diluted with 30 ml of chloroform, washed with 2% aqueous sodium bicarbonate and dried with sodium sulfate, and then, the solvent was evaporated. The residue was purified on a silica gel column (a product was eluted with 5% methanol : chloroform), and the solvent was evaporated to obtain a glassy compound (4) represented by the following formula:

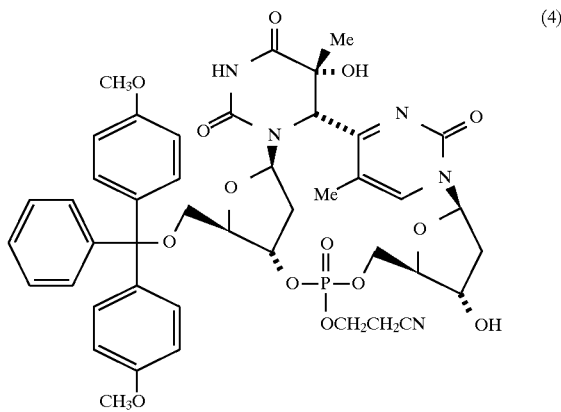

(4)

with $R_f$ 0.10 (chloroform:methanol=10:1) (disappearance of the levulinyl group was confirmed by $^1$H—NMR) (yielded

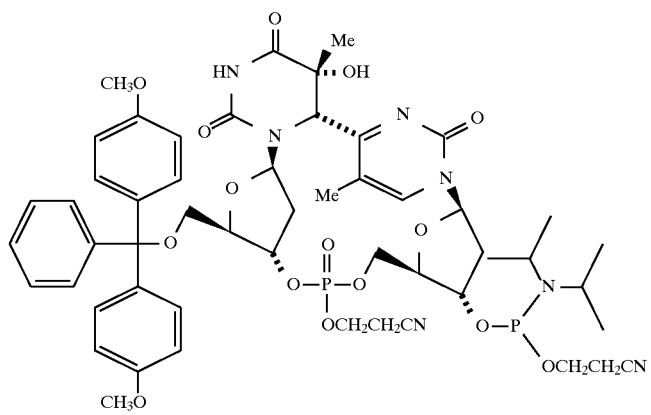

(5)

amount: 184 mg, 204 μmol, yield: 85%). The compound (4) was dissolved in 2.0 ml of pyridine, 142 μl (816 μmol) of N,N-diisopropylethylamine and 91 μl (408 μmol) of 2-cyanoethyl-N,N-diisopropylchlorophosphoramidite were added to the solution, and the mixture was stirred at room temperature for 30 minutes. Then, ethyl acetate was added to the mixture and the resulting mixture was washed with 2% aqueous sodium bicarbonate and a saturated sodium chloride solution and dried with sodium sulfate, and the solvent was evaporated. The residue was purified on a silica gel column (a product was eluted with 2% methanol chloroform containing 0.1% pyridine), and the solvent was evaporated. Then, the residue was dissolved in chloroform, and the solution was added dropwise to pentane. The resulting precipitates were dissolved again in chloroform, and the solvent was evaporated to obtain a title compound (5) as a foamy product.

Yielded amount: 149 mg (135 μmol, yield: 66%) TLC (chloroform : methanol=10:1): $R_f$ 0.41 $^1$H—NMR (600 MHz, pyridine-$d_5$) δ (ppm) : 8.47 (s, 1H, —NH—) 7.93 (s, 1H, pT H6), 7.85 (d, J=6.73 Hz, 1H, aromatic ring), 7.84 (d, J=6.26 Hz, 1H, aromatic ring), 7.71 (d, J=7.37 Hz, 2H, aromatic ring), 7.69 (d, J=7.25Hz, 2H, aromatic ring), 7.48 (dd, J=7.74, 7.74 Hz, 2H, aromatic ring), 7.33 (dd, J=7.05, 7.05 Hz, 1H, aromatic ring), 7.07 (d, J=5.38 Hz, 4H, aromatic ring), 6.86 (br s, 1H, pT H1'), 6.82 (d, J=7.42 Hz, 1H, Tp H1'), 5.02 (m, 1H, pT H3'), 4.37 (m, 1H, Tp H3'), 4.34 to 4.20 (m, 5H, Tp H4', pT H4', —OH, —OCH$_2$CH$_2$CN) , 3.95 (m, 2H, Tp H5', —OCH$_2$CH$_2$CN× ½*), 3.75 (s, 6H, —OCH$_3$), 3.72 (m, 2H, Tp H5", —OCH$_2$CH$_2$CN×½*), 3.61 (m, 2H, —CH(CH$_3$)$_2$), 3.12 to 2.92 (m, 6H, pT H2', H5', —OCH$_2$CH$_2$CN×2), 2.89*, 2.80* (m, 1H, pT H5"), 2.72*, 2.62* (m, 1H, pT H2"), 2.36*, 2.32* (s, 3H, pT —CH$_3$), 2.27 (m, 1H, Tp H2"), 2.14 (m, 1H, Tp H2'), 1.96 (s, 3H, Tp —CH$_3$), 1.17 (d, J=7.00 Hz, 6H, —CH(CH$_3$)$_2$), 1.16 (d, J=7.00 Hz, 6H, —CH(CH$_3$)$_2$) * represents isomers. $^{31}$P—NMR (121.5 MHz, pyridine-$d_5$) δ: 145.78, −4.16, −4.44 ppm Example 2

Preparation of (6-4) 8-mer

The compound (5) obtained in Example 1 (iii) (143 mg (130 μmol)) was dissolved in 1.0 ml of acetonitrile and installed on the DNA synthesizer. By using 0.2 μmol of deoxyguanosine-CPG (controlled pore glass) column (trade name, manufactured by PerSeptive Biosystems), d(GTAT (6-4)TATG), SEQ ID NO.2, was synthesized. The reaction time for the coupling of the compound (5) was prolonged to 20 minutes. After completion of the synthesis, the solid support to which the oligonucleotide was linked was treated with about 2 ml of 28% aqueous ammonia at room temperature for 2 hours. Then, aqueous ammonia was evaporated, the residue was dissolved in 1.0 ml of distilled water, and an aliquot of the solution was analyzed by reverse-phase HPLC. A main product having an absorption maximum at 326 nm was eluted with a linear gradient of 7 to 11% aqueous acetonitrile for 20 minutes, at a retention time of 11.2 minutes. This peak perfectly coincided with that of a product obtained by UV irradiation of an 8-mer having no photoproduct (d(GTATTATG)). This product was subjected to purification by reverse-phase HPLC to obtain 6.8 $A_{260}$ units of the desired product.

Example 3

Preparation of (6-4) 30-mer

By the similar method as for the (6-4) 8-mer in Example 2, d(CTCGTCAGCATCT(6-4) TCATCATACAGTCAGTG), SEQ ID NO.1, was synthesized. When an aliquot was analyzed by reverse-phase HPLC, a main product having an absorption maximum at 327 nm was eluted with a linear gradient of 7 to 13% acetonitrile for 20 minutes, at a retention time of 12.5 minutes. When the product was analyzed by an anion-exchange HPLC, it perfectly coincided with a 30-mer containing no photoproduct (d(CTCGTCAGCATCTTCATCATACAGTCAGTG, SEQ ID NO.3)). This product was subjected to purification by reverse-phase HPLC to obtain 6.0 $A_{260}$ units of the desired product.

What is claimed is:

1. A coupling unit of a (6-4) photoproduct represented by the formula (I):

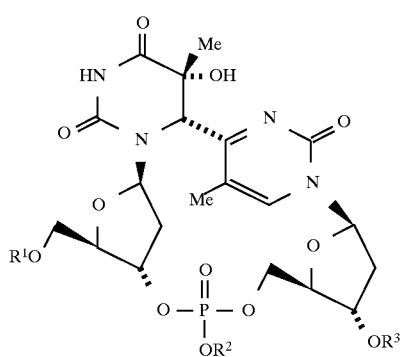

wherein $R^1$ represents a protective group, $R^2$ represents a methyl group or a 2-cyanoethyl group, and $R^3$ represents

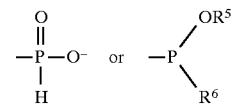

wherein $R^5$ represents a methyl group or a 2-cyanoethyl group, and $R^6$ represents a —(R')(R") group, a N-morpholino group, a N-pyrrolidinyl group or a 2,2,6,6-tetramethyl-N-piperidyl group where R' and R" each represent a lower alkyl group.

2. The coupling unit according to claim 1, wherein $R^1$ is a 4,4'-dimethoxytrityl group, $R^2$ is a 2-cyanoethyl group, and $R^3$ is a 2-cyanoethyl-N,N-dialkylphosphoramidite group.

3. A coupling unit of a (6-4) photoproduct represented by the formula (2):

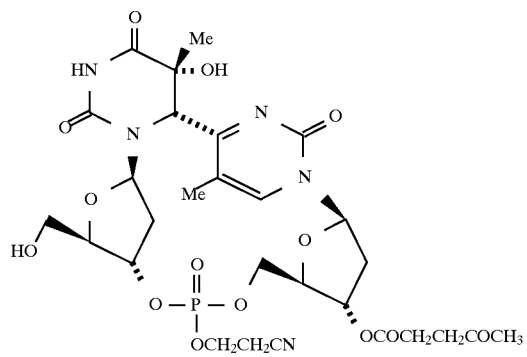

wherein Me means a methyl group.

4. A coupling unit of a (6-4) photoproduct represented by the formula (3):

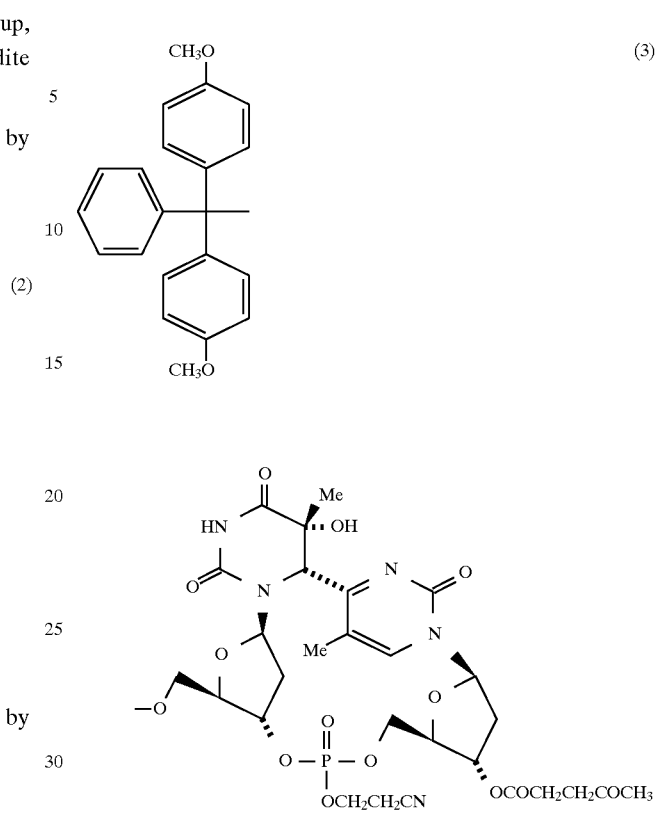

wherein Me means a methyl group.

5. The coupling unit according to claim 1, wherein said unit is represented by the formula (5):

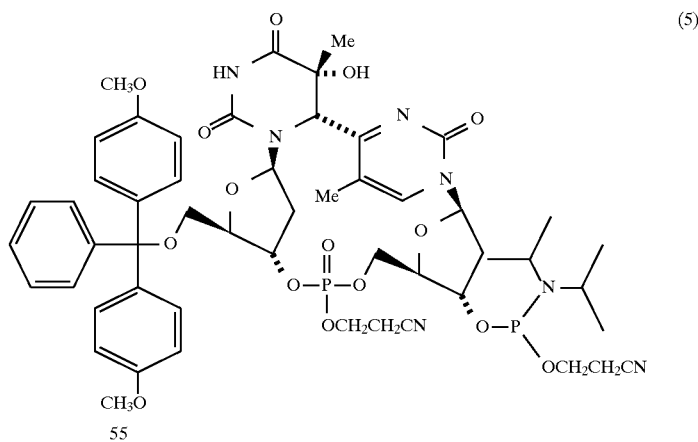

wherein Me means a methyl group.

6. A process for preparing the coupling unit of the (6-4) photoproduct with the formula (I) according to claim 1, which comprises reacting a compound represented by the formula (V):

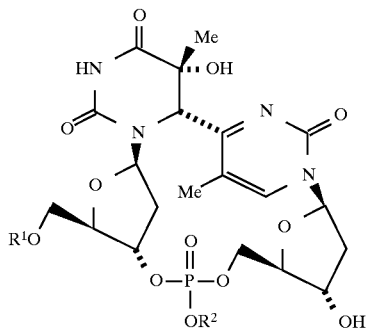
(V)

wherein $R^1$ represents a protective group, and $R^2$ represents a methyl group or a 2-cyanoethyl group with a compound represented by

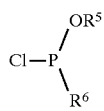

wherein $R^5$ represents a methyl group or a 2-cyanoethyl group, and $R^6$ represents a —N(R')(R") group, a N-morpholino group, a N-pyrrolidinyl group or a 2,2,6,6-tetramethyl-N-piperidyl group where R' and R" each represent a lower alkyl group, or reacting the compound represented by the formula (V) with tri(1,2,4-triazol-1-yl)phosphine, followed by hydrolysis.

7. The process according to claim 6, wherein $R^1$ is a 4,4'-dimethoxytrityl group, $R^2$ is a 2-cyanoethyl group, and $R^3$ is a 2-cyanoethyl-N,N-dialkylphosphoramidite group.

8. A process for preparing the coupling unit of the (6-4) photoproduct with the formula (I) according to claim 1, which comprises:

(1) irradiating a thymidine dimer represented by the formula (II):

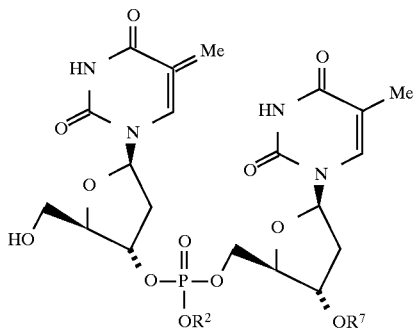
(II)

wherein $R^2$ represents a methyl group or a 2-cyanoethyl group, and $R^7$ represents a levulinyl group or a t-butyldimethylsilyl group with UV light to obtain a (6-4) photoproduct represented by the formula (III):

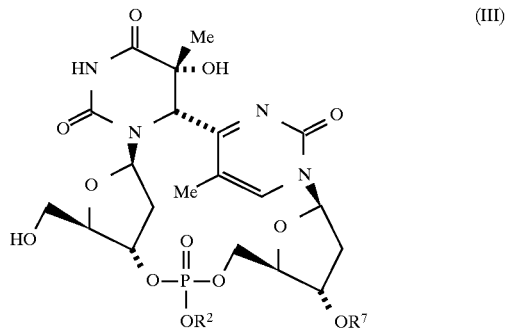
(III)

wherein $R^2$ and $R^7$ are the same as defined above;

(2) protecting the 5'—OH group to prepare a compound with the formula (IV):

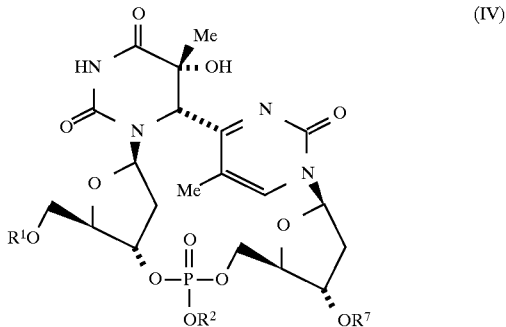
(IV)

wherein $R^1$ represents a protective group, and $R^2$ and $R^7$ are the same as defined above;

(3) removing the protective group $R^7$ for the 3'—OH to obtain a compound with the formula (V):

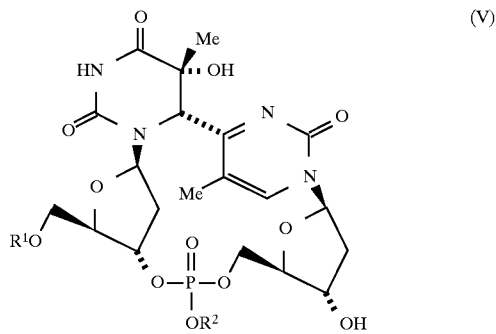
(V)

wherein $R^1$ and $R^2$ are the same as defined above; and (4) reacting the compound represented by the formula (V) with a compound represented by

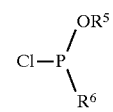

wherein $R^5$ represents a methyl group or a 2-cyanoethyl group, and $R^6$ represents a —N(R')(R") group, a N-morpholino group, a N-pyrrolidinyl group or a 2,2,6,6-tetramethyl-N-piperidyl group where R' and R" each represent a lower alkyl group, or reacting the compound represented by the formula (V) with tri(1,2,4-triazol-1-yl)phosphine, followed by hydrolysis.

9. The process according to claim 8, wherein $R^1$ is a 4,4'-dimethoxytrityl group, $R^2$ is a 2-cyanoethyl group, $R^3$ is a 2-cyanoethyl-N,N-dialkylphosphoramidite group, and $R^7$ is a levulinyl group.

10. A process for preparing an oligonucleotide containing a (6-4) photoproduct represented by the formula (X):

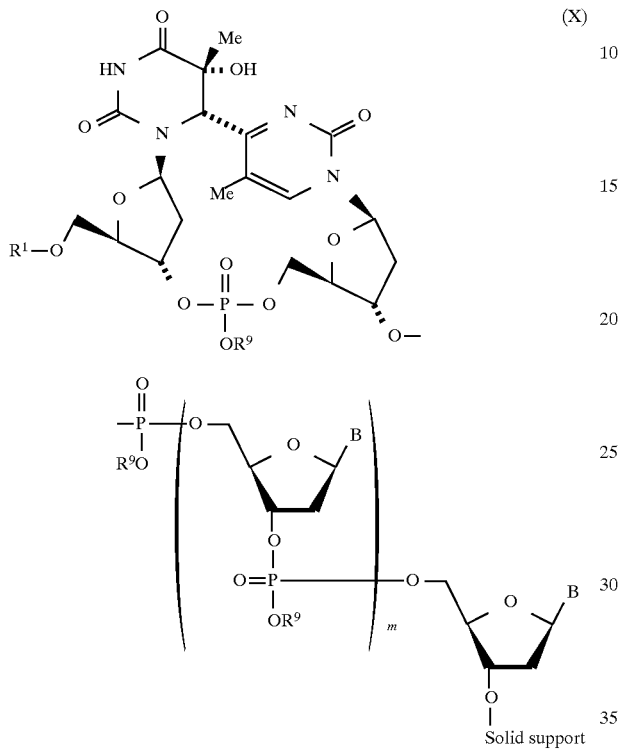
(X)

wherein $R^1$ represents a protective group, $R^9$ represents a hydrogen atom, a methyl group or a 2-cyano-ethyl group, B represents

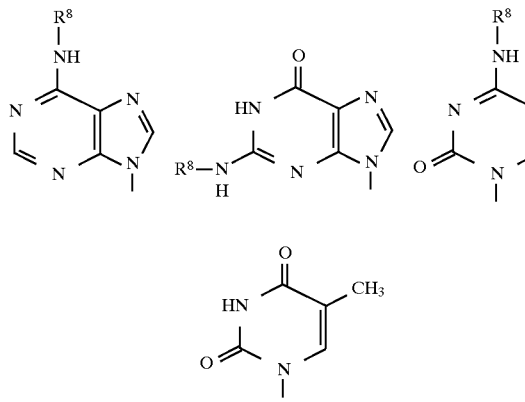

where $R^8$ represents a protective group,
and m represents 1 to 30, which comprises:

(1) removing the protective group $R^1$ on an oligonucleotide linked to a solid support, represented by the formula (IX):

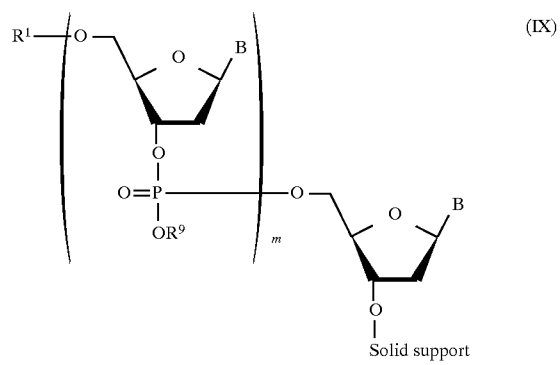
(IX)

wherein $R^1$, $R^9$, B and m are the same as defined above;

(2) reacting the oligonucleotide with a coupling unit of a (6-4) photoproduct represented by the formula (I):

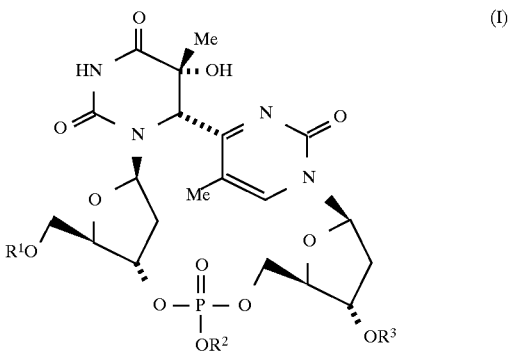
(I)

wherein $R^1$ is the same as defined above, $R^2$ represents a methyl group or a 2-cyanoethyl group, and $R^3$ represents

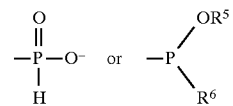

wherein $R^5$ represents a methyl group or a 2-cyanoethyl group, and $R^6$ represents a —N(R')(R") group, a N-morpholino group, a N-pyrrolidinyl group or a 2,2,6,6-tetramethyl-N-piperidyl group where R' and R" each represent a lower alkyl group;
and (3) oxidizing the reaction mixture.

11. The process according to claim 10, wherein $R^1$ is a 4,4'-dimethoxytrityl group, $R^3$ is a 2-cyanoethyl-N,N-dialkylphosphoramidite group, $R^8$ is a t-butylphenoxyacetyl group, and $R^9$ is a 2-cyanoethyl group.

12. A process for preparing DNA containing a (6-4) photo-product represented by the formula (XII):

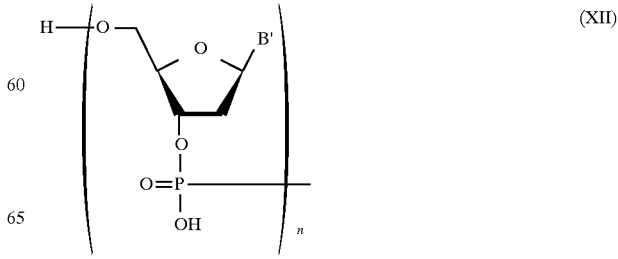
(XII)

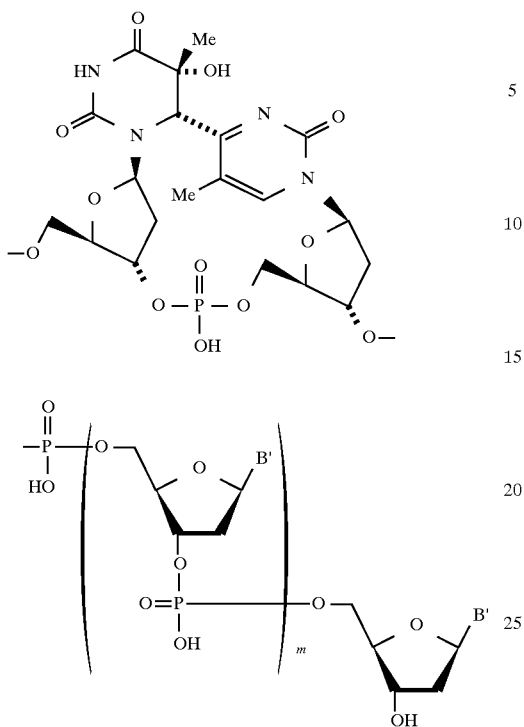

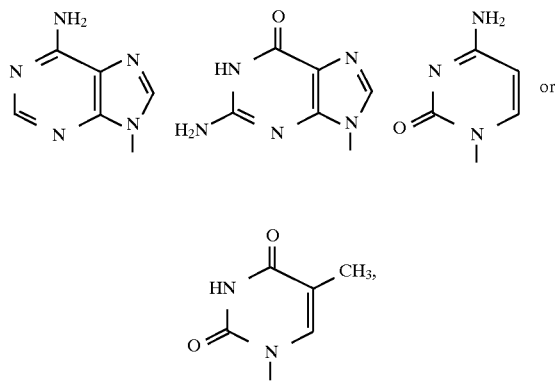

wherein B' represents

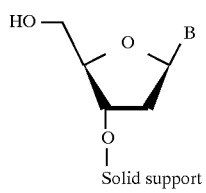

m represents 1 to 30, and n represents 1 to 30, which comprises:

(1) reacting a nucleoside linked to a solid support, represented by the formula (VII):

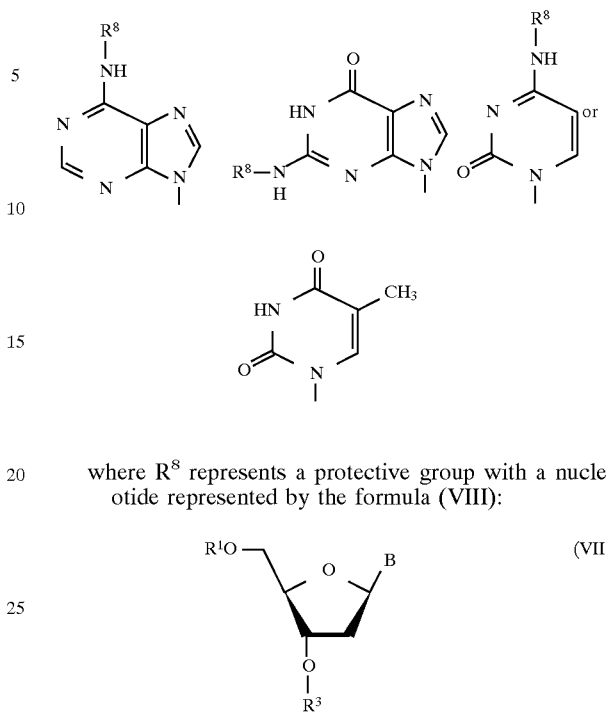

wherein B represents

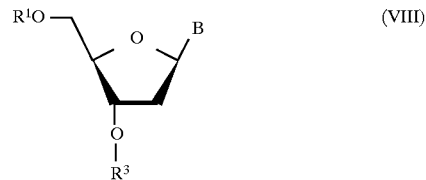

where $R^8$ represents a protective group with a nucleotide represented by the formula (VIII):

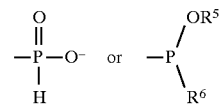

wherein $R^1$ represents a protective group, $R^3$ represents $$-\overset{O}{\underset{H}{\overset{\|}{P}}}-O^- \quad \text{or} \quad -P\overset{OR^5}{\underset{R^6}{\diagdown}}$$

wherein $R^5$ represents a methyl group or a 2-cyanoethyl group, and $R^6$ represents a —N(R')(R") group, a N-morpholino group, a N-pyrrolidinyl group or a 2,2,6,6-tetramethyl-N-piperidyl group where R' and R" each represent a lower alkyl group, and B is the same as defined above, oxidizing the reaction mixture and repeating removal of $R^1$, the above reaction and oxidation to obtain an oligonucleotide represented by the formula (IX):

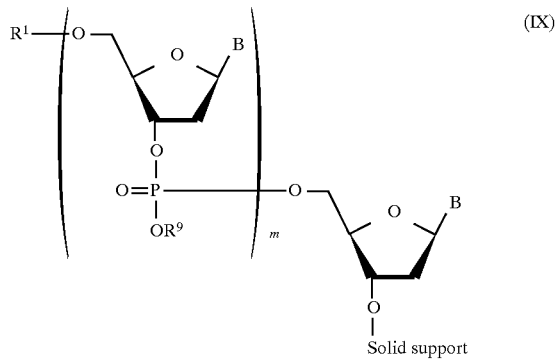

wherein $R^9$ represents a hydrogen atom, a methyl group or a 2-cyanoethyl group, and $R^1$, B, and m are the same as defined above;

(2) after removing the protective group $R^1$, reacting the oligonucleotide with the coupling unit of a (6-4) photoproduct represented by the formula (I):

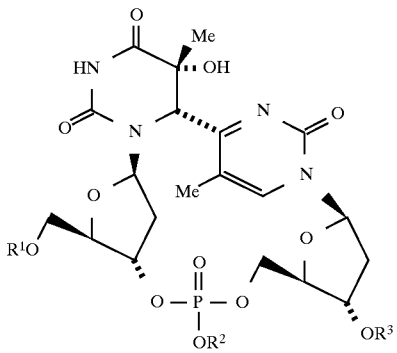

wherein $R^2$ represents a methyl group or a 2-cyanoethyl group, and $R^1$ and $R^3$ are the same as defined above, and oxidizing the reaction mixture to obtain an oligonucleotide containing a (6-4) photoproduct represented by the formula (X):

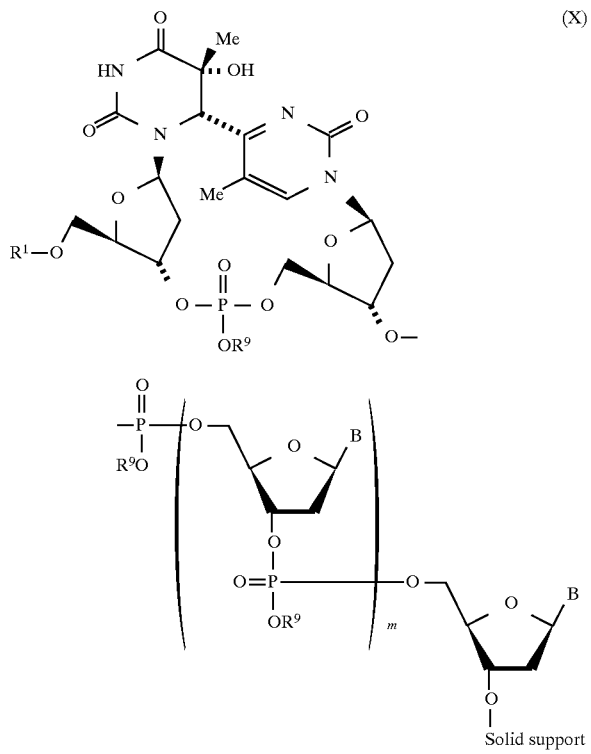

wherein $R^1$, $R^9$, B and m are the same as defined above;

(3) after removing the protective group $R^1$, reacting the oligonucleotide with the nucleotide represented by the formula (VIII), oxidizing the reaction mixture and repeating the reaction and oxidation to obtain an oligonucleotide containing a (6-4) photoproduct represented by the formula (XI):

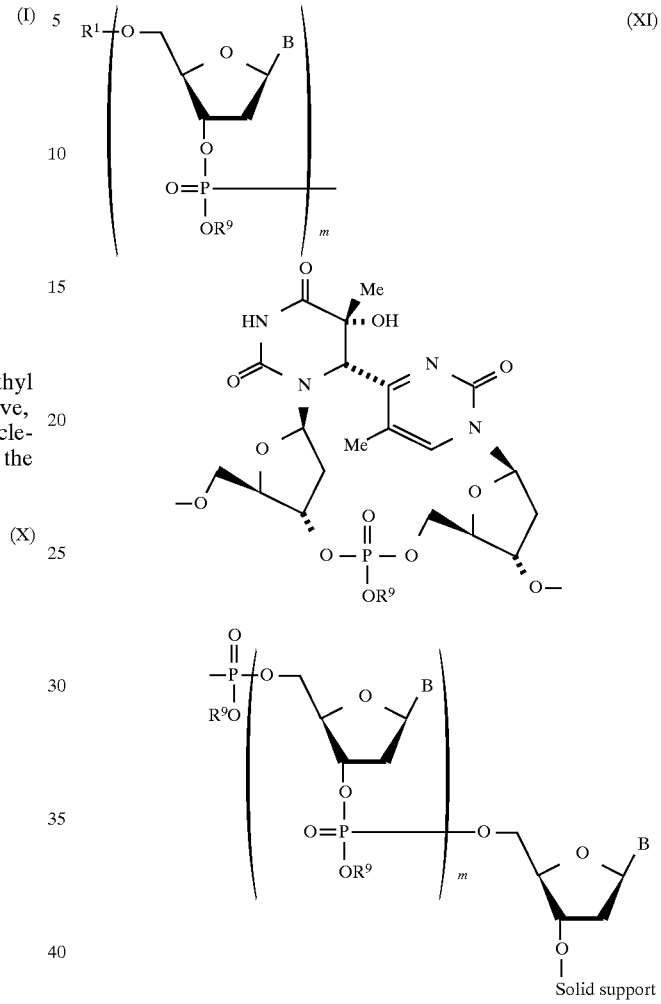

wherein $R^1$, $R^9$, B, m and n are the same as defined above; and (4) after taking off the protective group $R^1$, treating the long oligonucleotide with aqueous ammonia to remove the protective groups $R^9$ and $R^8$ and simultaneously to cleave the long oligonucleotide from the solid support.

13. The process according to claim 12, wherein $R^1$ is a 4,4'-dimethoxytrityl group, $R^3$ is a 2-cyanoethyl-N,N-dialkylphosphoramidite group, $R^8$ is a t-butylphenoxyacetyl group, and $R^9$ is a 2-cyanoethyl group.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 30 nucleic acids
        ( B ) TYPE: nucleic acid
        ( C ) STRANDEDNESS: single strand
        ( D ) TOPOLOGY: linear ( i x ) FEATURE:
        ( B ) LOCATION: 13 to 14
        ( D ) OTHER INFORMATION: the sequence contains a pyrimidine
            ( 6 - 4 ) pyrimidone bond between bases of nucleotides 13 and
            14

( x ) PUBLICATION INFORMATION:
        ( A ) AUTHORS: Shigenori IWAI
        ( B ) TITLE: COUPLING UNIT OF (6-4) PHOTOPRODUCT, PROCESS FOR
            PREPARING THE SAME, PROCESS FOR PREPARING
            OLIGONUCLEOTIDE CONTAINING (6-4) PHOTOPRODUCT BY
            USING THE SAME AND PROCESS FOR PREPARING DNA
            CONTAINING (6-4) PHOTOPRODUCT BY USING THE SAME
        ( K ) RELEVANT RESIDUES IN SEQ ID NO:1: FROM 1 to 30

( x i ) SEQUENCE DESCRIPTION: SEQ ID NO:1:

CTCGTCAGCA TCTTCATCAT ACAGTCAGTG                                                                      30

( 2 ) INFORMATION FOR SEQ ID NO: 2:

( i ) SEQUENCE CHARACTERISTICS:
        ( A ) LENGTH: 8 nucleic acids
        ( B ) TYPE: nucleic acid
        ( C ) STRANDEDNESS: single strand
        ( D ) TOPOLOGY: linear ( i x ) FEATURE:
        ( B ) LOCATION: 4 to 5
        ( D ) OTHER INFORMATION: the sequence contains a pyrimidine
            ( 6 - 4 ) pyrimidone bond between bases of nucleotides 4 and 5

( x ) PUBLICATION INFORMATION:
        ( A ) AUTHORS: Shigenori IWAI
        ( B ) TITLE: COUPLING UNIT OF (6-4) PHOTOPRODUCT, PROCESS FOR
            PREPARING THE SAME, PROCESS FOR PREPARING
            OLIGONUCLEOTIDE CONTAINING (6-4) PHOTOPRODUCT BY
            USING THE SAME AND PROCESS FOR PREPARING DNA
            CONTAINING (6-4) PHOTOPRODUCT BY USING THE SAME
        ( K ) RELEVANT RESIDUES IN SEQ ID NO:2: FROM 1 to 8

( x i ) SEQUENCE DESCRIPTION: SEQ ID NO:2:

GTATTATG                                                                                                8

( 2 ) INFORMATION FOR SEQ ID NO: 3:

( i ) SEQUENCE CHARACTERISTICS:
        ( A ) LENGTH: 30 nucleic acids
        ( B ) TYPE: nucleic acid
        ( C ) STRANDEDNESS: single strand
        ( D ) TOPOLOGY: linear ( x ) PUBLICATION INFORMATION:
        ( A ) AUTHORS: Shigenori IWAI
        ( B ) TITLE: COUPLING UNIT OF (6-4) PHOTOPRODUCT, PROCESS FOR
            PREPARING THE SAME, PROCESS FOR PREPARING
            OLIGONUCLEOTIDE CONTAINING (6-4) PHOTOPRODUCT BY
            USING THE SAME AND PROCESS FOR PREPARING DNA
            CONTAINING (6-4) PHOTOPRODUCT BY USING THE SAME
        ( K ) RELEVANT RESIDUES IN SEQ ID NO:3: FROM 1 to 30

( x i ) SEQUENCE DESCRIPTION: SEQ ID NO:3:

CTCGTCAGCA TCTTCATCAT ACAGTCAGTG                                                                      30